(12) United States Patent
Sheng et al.

(10) Patent No.: US 6,489,627 B1
(45) Date of Patent: Dec. 3, 2002

(54) METHOD FOR INSPECTING A RETICLE AND APPARATUS FOR USE THEREIN

(75) Inventors: Parson Sheng; Cheng-Hsun Lin; Joseph Guo, all of Hsin-Chu (TW)

(73) Assignee: Taiwan Semiconductor Manufacturing Co., Ltd, Hsin Chu (TW)

( * ) Notice: Subject to any disclaimer, the term of this patent is extended or adjusted under 35 U.S.C. 154(b) by 66 days.

(21) Appl. No.: 09/675,929

(22) Filed: Sep. 29, 2000

(51) Int. Cl.$^7$ ............................................... G01N 21/86
(52) U.S. Cl. ................. 250/559.4; 250/559.3; 356/237.4
(58) Field of Search ........................... 250/559.4, 559.3, 250/559.44, 559.11; 356/237.4, 237.1, 237.5, 238.1, 239.1, 239.3

(56) References Cited

U.S. PATENT DOCUMENTS 5,098,191 A    3/1992  Noguchi et al.
5,481,362 A *  1/1996  Van Den Brink et al. .. 356/401
5,737,072 A    4/1998  Emery et al.

* cited by examiner

Primary Examiner—Que T. Le
(74) Attorney, Agent, or Firm—Tung & Associates

(57) ABSTRACT

Within each of: (1) a method for inspecting a reticle; (2) an apparatus for inspecting the reticle; and (3) a method for forming a microelectronic layer while employing the method for inspecting the reticle and the apparatus for inspecting the reticle, there is employed a pair of wedges whose inclined surfaces are counter-opposed and separated by a gap. The pair of wedges whose inclined surfaces are counter-opposed and separated by the gap is employed in conjunction with an inspection light source and detector for determining an optimizing an optical characteristic of the reticle, such as an optimized optical interference characteristic of the reticle, such that the reticle may be optimally aligned within a photoexposure apparatus and there may be formed with optimal registration while employing the reticle and the photoexposure apparatus a microelectronic layer within a microelectronic fabrication.

16 Claims, 1 Drawing Sheet

METHOD FOR INSPECTING A RETICLE AND APPARATUS FOR USE THEREIN

BACKGROUND OF THE INVENTION

1. Field of the Invention

The present invention relates generally to reticles employed when fabricating microelectronic fabrications. More particularly, the present invention relates to methods and apparatus for inspecting reticles employed when fabricating microelectronic fabrications.

2. Description of the Related Art

Microelectronic fabrications are formed from microelectronic substrates over which are formed patterned microelectronic conductor layers which are separated by microelectronic dielectric layers.

As microelectronic fabrication integration levels have increased and microelectronic device and patterned microelectronic conductor layer dimensions have decreased, it has become increasingly important when fabricating microelectronic fabrications to assure optimal registration of various overlying microelectronic layers which may be employed when fabricating a microelectronic fabrication.

While assuring optimal registration of various overlying microelectronic layers which may be employed when fabricating a microelectronic fabrication is thus clearly of significance and importance when fabricating a microelectronic fabrication, assuring optimal registration of various overlying microelectronic layers which may be employed when fabricating a microelectronic fabrication is nonetheless not entirely without problems in the art of microelectronic fabrication. In that regard, it is often recognized in the art of microelectronic fabrication that optimal registration of various overlying layers which may be employed when fabricating a microelectronic fabrication may be influenced by multiple interrelated and obscure factors derived from interactions between a photoexposure reticle and a photoexposure apparatus.

It is thus in general towards the goal of providing optimal registration of various overlying layers which may be employed when fabricating a microelectronic fabrication that the present invention is generally directed. Similarly, it is thus more particularly towards the goal of providing an efficient method for inspecting a reticle such as to provide optimal registration of an overlying layer which may be employed when fabricating a microelectronic fabrication while employing the reticle that the present invention is more specifically directed.

Various methods and apparatus have been disclosed in the art of microelectronic fabrication for inspecting reticles employed within the art of microelectronic fabrication.

For example, Noguchi et al., in U.S. Pat. No. 5,098,191, discloses a method for inspecting a reticle and a related apparatus for inspecting the reticle, wherein only foreign substances and defects which actually produce damage when employing the reticle incident to forming a microelectronic layer for use within a microelectronic fabrication are detected. To realize the foregoing object, the method for inspecting the reticle and the apparatus for inspecting the reticle employ a comparison of an inspected reticle in conjunction with a standard reticle with respect to reflected illuminating inspection light characteristics and transmitted illuminating inspection light characteristics.

In addition, Emery et al., in U.S. Pat. No. 5,737,072, discloses a method for inspecting a reticle and a apparatus for inspecting the reticle, wherein the method for inspecting the reticle and the apparatus for inspecting the reticle need not employ a standard reticle for comparison purposes when inspecting the reticle while employing the method for inspecting the reticle and the apparatus for inspecting the reticle. To realize the foregoing result, defect detection within the reticle is determined while employing the method for inspecting the reticle and the apparatus for inspecting the reticle by comparing combinations of at least two inspection light transmission signals or light reflection signals which are measured or derived while employing the method for inspecting the reticle and the apparatus for inspecting the reticle.

Desirable in the art of microelectronic fabrication are additional methods and apparatus which may be employed for inspecting reticles employed for fabricating microelectronic fabrications, particularly as regards inspecting reticles such as to assure optimal registration of overlying layers within microelectronic fabrications which are fabricated while employing the reticles.

It is towards the foregoing object that the present invention is directed.

SUMMARY OF THE INVENTION

A first object of the present invention is to provide a method for inspecting a reticle and an apparatus for inspecting the reticle.

A second object of the present invention is to provide the method for inspecting the reticle and the apparatus for inspecting the reticle in accord with the first object of the present invention, wherein the method for inspecting the reticle and the apparatus for inspecting the reticle provide for optimal registration of an overlying layer within a microelectronic fabrication fabricated employing the reticle.

A third object of the present invention is to provide the method for inspecting the reticle and the apparatus for inspecting the reticle in accord with the first object of the invention and the second object of the invention, which method and apparatus are readily commercially implemented.

In accord with the objects of the present invention, there is provided by the present invention a method for inspecting a reticle and an apparatus for inspecting the reticle. To practice the method for inspecting the reticle, there is first provided a reticle comprising a transparent substrate having formed thereupon a patterned non-transparent layer which defines an alignment mark. There is then impinged at a non-orthogonal angle through the alignment mark within the reticle an inspection light beam which is both: (a) refracted and transmitted directly through the reticle; and (b) refracted, reflected and then transmitted through the reticle, to thus provide a multiplicity of refracted transmitted inspection light beams. There is then passed the multiplicity of refracted transmitted inspection light beams through a pair of wedges whose inclined surfaces are counter-opposed and separated by a gap to form a multiplicity of additionally refracted transmitted inspection light beams. Finally, there is then varied a distance of the gap to optimize an optical characteristic of the additionally refracted transmitted inspection light beams.

Optionally, the method for inspecting the reticle may also further comprise correlating a variation of the distance of the gap to a variation of the non-orthogonal angle to provide a varied non-orthogonal angle which alternatively optimizes an optical characteristic of the additionally refracted transmitted inspection light beams.

The method for inspecting the reticle in accord with the present invention contemplates an apparatus for inspecting the reticle in accord with the present invention.

In addition, the method for inspecting the reticle in accord with the present invention also contemplates a method for aligning the reticle within a photoexposure apparatus in accord with the present invention.

The present invention provides a method for inspecting a reticle and an apparatus for inspecting the reticle, wherein the method for inspecting the reticle and the apparatus for inspecting the reticle provide for optimal registration of an overlying layer within a microelectronic fabrication fabricated employing the reticle. The method for inspecting the reticle and the apparatus for inspecting the reticle in accord with the present invention realize the foregoing object by employing with respect to a multiplicity of refracted transmitted inspection light beams derived from an inspection light beam incident non-orthogonal to a reticle at the location of an alignment mark within the reticle a pair of transparent wedges whose inclined surfaces are counter-opposed and separated by a gap a distance of which is varied to optimize an optical characteristic of a series of additionally refracted transmitted inspection light beams derived from the series of refracted transmitted inspection light beams. Similarly, within the method for inspecting the reticle and the apparatus for inspecting the reticle of the present invention there is optionally correlated a distance of the gap with a variation of the non-orthogonal angle in a fashion which alternatively optimizes the optical characteristic of the additionally refracted transmitted inspection light beams and thus contributes to enhanced alignment of the reticle within a photoexposure apparatus and thus enhanced registration of a microelectronic layer formed within a microelectronic fabrication while employing the reticle and the photoexposure apparatus.

The method for inspecting the reticle and the apparatus for inspecting the reticle are readily commercially implemented. The method for inspecting the reticle in accord with the present invention and the apparatus for inspecting the reticle in accord with the present invention employ sub-methods, materials and components as are generally known in the art of microelectronic fabrication, but employed and/or fabricated in a fashion which provides the present invention. Since it is thus a specific configuration of process steps and/or components which provides at least in part the present invention, rather than the existence of methods, materials and components which provides the present invention, the method of the present invention and the apparatus of the present invention are readily commercially implemented.

BRIEF DESCRIPTION OF THE DRAWINGS

The objects, features and advantages of the present invention are understood within the context of the Description of the Preferred Embodiment, as set forth below. The Description of the Preferred Embodiment is understood within the context of the accompanying drawings, which form a material part of this application, wherein.

DESCRIPTION OF THE PREFERRED EMBODIMENT

The present invention provides a method for inspecting a reticle and an apparatus for inspecting the reticle, wherein the method for inspecting the reticle and the apparatus for inspecting the reticle provide, when employing the reticle within a photoexposure apparatus, for optimal registration of various overlying microelectronic layers which may be employed when fabricating a microelectronic fabrication. The method for inspecting the reticle in accord with the present invention and the apparatus for inspecting the reticle in accord with the present invention realize the foregoing object by employing with respect to a multiplicity of refracted transmitted inspection light beams derived from an inspection light beam non-orthogonal to the reticle at the location of an alignment mark within the reticle a pair of transparent wedges whose inclined surfaces are counter-opposed and separated by a gap a distance of which is varied to optimize an optical characteristic of a series of additionally refracted transmitted inspection light beams derived from the series of refracted transmitted inspection light beams. Similarly, within the method and apparatus of the present invention there is correlated a distance of the gap with a variation of the non-orthogonal angle in a fashion which alternatively optimizes the optical characteristic of the additionally refracted transmitted inspection light beams and thus allows for enhanced alignment of the reticle within a photoexposure apparatus.

Within the present invention, the reticle which is inspected in accord with the method for inspecting the reticle and the apparatus for inspecting the reticle may in turn be employed for fabricating a microelectronic fabrication selected from the group including but not limited to an integrated circuit microelectronic fabrication, a ceramic substrate microelectronic fabrication, a solar cell optoelectronic microelectronic fabrication, a sensor image array optoelectronic microelectronic fabrication and a display image array optoelectronic microelectronic fabrication.

Figure 1:
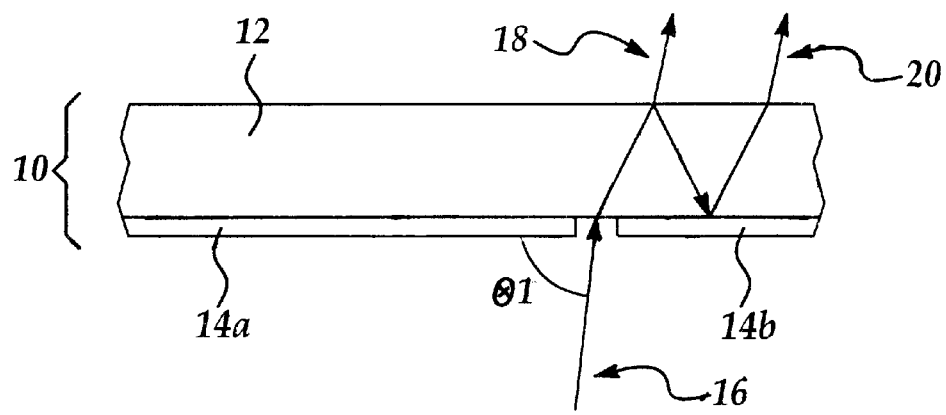
FIG. 1 shows a schematic cross-sectional diagram of a reticle whose alignment registration within a photoexposure apparatus may be enhanced in accord with the present invention.

Referring now to FIG. 1, there is shown a schematic cross-sectional diagram illustrating a reticle which may be inspected employing the method of the present invention and the apparatus of the present invention.

Shown in FIG. 1 is a reticle 10 comprising a transparent substrate 12 having formed thereupon a pair of patterned non-transparent layers 14a and 14b which define an aperture which serves as an alignment mark within the reticle 10. The aperture which serves as the alignment mark within the reticle 10 whose schematic cross-sectional diagram is illustrated in FIG. 1 may have any shape as is conventionally employed when forming an alignment mark within a reticle employed for fabricating a microelectronic fabrication, such shapes including but not limited to square shapes, rectangular shapes, circular shapes and cross shapes.

Within the preferred embodiment of the present invention with respect to the transparent substrate 12, the transparent substrate 12 may be formed from any of several transparent materials from which may be formed transparent substrates which are employed within reticles, such transparent materials being selected from the group including but not limited to transparent quartz materials and transparent glass materials. Typically and preferably, the transparent substrate 12 is formed of a transparent quartz material formed to a thickness of from about 6400 to about 6600 $\mu$m.

Similarly, within the preferred embodiment of the present invention with respect to the pair of patterned non-transparent layers 14a and 14b, the pair of patterned non-transparent layers 14a and 14b may analogously be formed employing any of several non-transparent materials as are conventionally employed for forming patterned non-transparent layers which define at least in part alignment marks within reticles, such non-transparent materials typically and preferably being selected from the group including but not limited to metals and metal alloys, with chromium metal being particularly common. Typically and preferably, the pair of patterned non-transparent layers 14a and 14b is formed of chromium metal formed to a thickness of from about 250 to about 275 angstroms.

Finally, there is also shown within the schematic cross-sectional diagram of FIG. 1 an incident alignment light beam 16 which is employed within a photoexposure apparatus for aligning the reticle 10 whose schematic cross-sectional diagram is illustrated in FIG. 1 with respect to a substrate having formed thereover a blanket photoresist layer which is otherwise intended to be photoexposed while employing the reticle whose schematic cross-sectional diagram is illustrated in FIG. 1. Neither the photoexposure apparatus nor the substrate having formed thereover the blanket photoresist layer are illustrated within the schematic cross-sectional diagram of FIG. 1, but both the photoexposure apparatus and the substrate having formed thereover the blanket photoresist layer are otherwise conventional in the art of microelectronic fabrication.

As is illustrated within the schematic cross-sectional diagram of FIG. 1, the incident alignment light beam 16 is incident upon the reticle 10 at the location of the alignment mark non-orthogonally, typically and preferably with an angle θ1, as illustrated within the schematic cross-sectional diagram of FIG. 1, of from about 0 to about 0.5 degrees. Thus the incident alignment light beam 16 is initially refracted within the reticle due to a difference in index of refraction between air and the transparent material from which is formed the transparent substrate 12. As is further illustrated within the schematic cross-sectional diagram of FIG. 1, a first portion of the incident light beam which is refracted within the transparent substrate 12 is transmitted directly through the transparent substrate 12 to form a refracted transmitted alignment light beam 18 and a second portion of the incident alignment light beam 16 which is refracted within the transparent substrate 12 is further also internally reflected within the transparent substrate 12 prior to being transmitted therethrough to form a reflected refracted transmitted alignment light beam 20.

When aligning the reticle whose schematic cross-sectional diagram is illustrated in FIG. 1 within a photoexposure apparatus it is common to employ both the refracted transmitted alignment light beam 18 and the reflected refracted transmitted alignment light beam 20 for proper alignment within the photoexposure apparatus of the reticle 10 whose schematic cross-sectional diagram is illustrated in FIG. 1 with respect to a substrate having formed thereover a blanket photoresist layer which is desired to be photoexposed while employing the reticle whose schematic cross-sectional diagram is illustrated in FIG. 1.

However, due to optical interference effects with respect to the refracted transmitted alignment light beam 18 and the reflected refracted transmitted alignment light beam 20, even minor variations in thickness of the transparent substrate 12 may cause sufficient deviations of optical characteristics, and in particular optical interference characteristics, of the refracted transmitted alignment light beam 18 and the reflected refracted transmitted alignment light beam 20 such that alignment of the reticle 10 whose schematic cross-sectional diagram is illustrated in FIG. 1 is compromised with respect to the substrate having formed thereover the blanket photoresist layer, and thus consequently registration of overlying layers within a microelectronic fabrication which is fabricated while employing the reticle 10 is also compromised.

The present invention is thus directed towards inspecting for the variations of thickness of the transparent substrate 12 (typically within one-half of an incident alignment light beam wavelength) which may provide for optical deviations when aligning within a photoexposure apparatus the reticle 10 whose schematic cross-sectional diagram is illustrated in FIG. 1 and compensating for the variations of thickness of the transparent substrate 12 which may provide for optical deviations when aligning within a photoexposure apparatus the reticle 10 whose schematic cross-sectional diagram is illustrated in FIG. 1, since such variations in turn provide for compromised alignment of the reticle 10 whose schematic cross-sectional diagram is illustrated in FIG. 1 within the photoexposure apparatus and thus compromised registration of overlying layers within a microelectronic fabrication which is fabricated while employing reticle 10.

Figure 2:
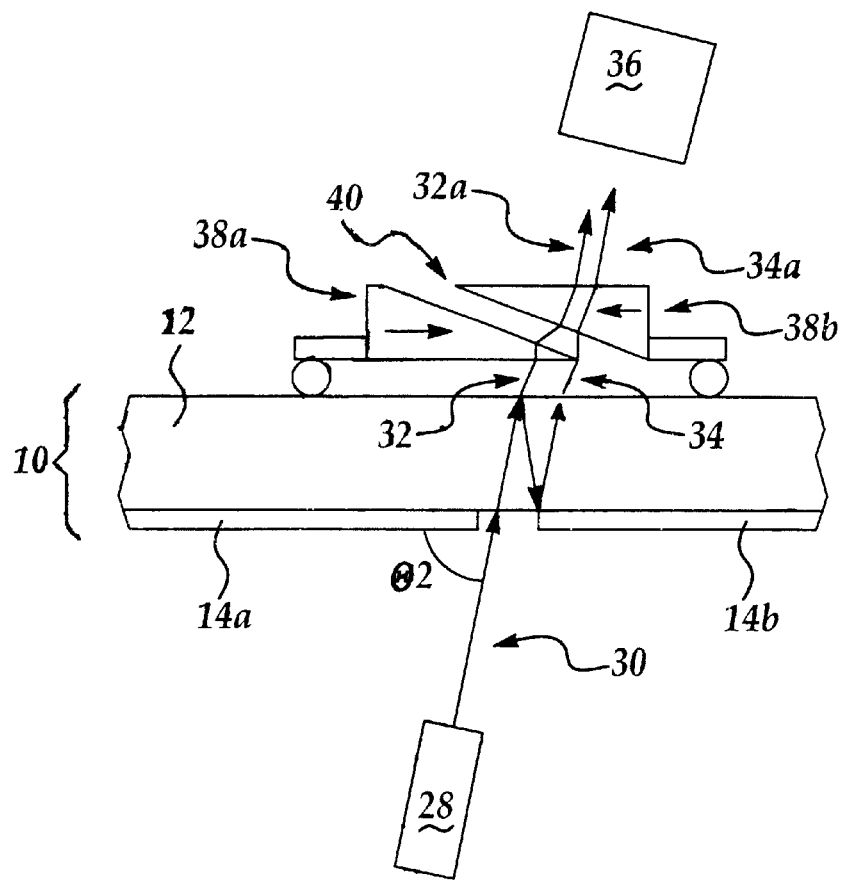
FIG. 2 shows a schematic cross-sectional diagram of the reticle as illustrated within FIG. 1, further wherein the reticle is positioned within an apparatus for inspecting the reticle in accord with the present invention.

Referring now to FIG. 2, there is shown an apparatus which may be employed in accord with the present invention for inspecting the reticle 10 in accord with the objects of the present invention.

Shown in FIG. 2 is the reticle 10 as is equivalent with the reticle 10 as illustrated within the schematic cross-sectional diagram of FIG. 1, but wherein there is now incident upon the alignment mark within the reticle which is defined by the pair of patterned non-transparent layers 14a and 14b which in part comprises the reticle 10 an incident inspection light beam 30 which is provided by an inspection light source 28.

Within the preferred embodiment of the present invention, the inspection light source 28 typically and preferably comprises a light source analogous or equivalent to the light source which provides the incident alignment light beam 16 as illustrated within the schematic cross-sectional diagram of FIG. 1. Thus, although any of several inspection light sources may be employed within the preferred embodiment of the present invention to provide the inspection light source 28 which in turn provides the incident inspection light beam 30, for the preferred embodiment of the present invention, the inspection light source 28 is typically and preferably a laser light source, more typically and preferably a 6328 angstrom wavelength helium-neon laser inspection light source, which provides the incident inspection light beam 30 more typically and preferably having a beam diameter of from about 20 to about 40 angstroms.

As is also illustrated within the schematic diagram of FIG. 2, and similarly with the incident alignment light beam 16 as illustrated within the schematic cross-sectional diagram of FIG. 1, the incident inspection light beam 30 as illustrated within the schematic cross-sectional diagram of FIG. 2 is incident upon the reticle 10 at the location of the alignment mark defined by the pair of patterned non-transparent layers 14a and 14b non-orthogonally at a non-orthogonal angle θ2 with respect to the transparent substrate 10 of from about 0 to about 0.5 degrees. Similarly, and also analogously within the incident alignment light beam 16 as illustrated within the schematic cross-sectional diagram of FIG. 1, a portion of the incident inspection light beam 30 is refracted within the transparent substrate 12 and transmitted directly through the transparent substrate 10 to form a refracted transmitted inspection light beam 32 while a separate portion of the incident inspection light beam 30 is further reflected within the transparent substrate 12 prior to being transmitted through the transparent substrate 12 as a reflected refracted transmitted inspection light beam 34.

As is further illustrated within the schematic diagram of FIG. 2, there is positioned horizontally spaced from the transparent substrate 12 surface of the reticle 10 as illustrated in FIG. 2 a pair of transparent wedges 38a and 38b whose inclined surfaces are counter-opposed and separated by a gap 40. As is further illustrated within the schematic cross-sectional diagram of FIG. 2, each of the pair of wedges 38a and 38b is independently movable such as to increase or decrease the gap 40 and as a result thereof each of the further refracted transmitted inspection light beam 32a and the further refracted reflected refracted transmitted inspection light beam 34a will have passed through an additional thickness of the wedges 38a and 38b. Each of the further refracted refracted transmitted inspection light beam 32a and the further refracted reflected refracted transmitted inspection light beam 34a is then detected with a detector 36 as is otherwise conventional in the art and specifically tuned to spatial and intensity characteristics of the further refracted refracted transmitted inspection light beam and the further refracted reflected refracted transmitted inspection light beam.

Within the preferred embodiment of the present invention with respect to each of the wedges 38a and 38b, each of the wedges 38a and 38b is typically and preferably formed of a transparent material of equivalent index of refraction as the index of refraction of the transparent material from which is formed the transparent substrate 12. Similarly, each of the wedges 38a and 38b typically and preferably has a projected length over the transparent substrate 12 of from about 6400 to about 6600 μm and a thickness perpendicular to the transparent substrate 12 of from about 6400 to about 6600 μm, while having a narrower angle of incline of from about 0 to about 0.5 degrees with respect to a surface which is parallel to the transparent substrate 12. In addition, the wedge 38a is typically and preferably spaced parallel from the transparent substrate 12 by a separation distance of from about 0.1 to about 10 millimeters and the gap 40 is typically and preferably continuously variable over a separation distance of from about 0.001 to about 0.70 millimeters. Finally, each of the exposed surfaces of the pair of wedges 38a and 38b through which passes the refracted transmitted inspection light beam 32 and the reflected refracted transmitted inspection light beam 34 typically and preferably has formed thereupon an anti-reflective coating (ARC) of a composition and thickness which is otherwise conventional in the art of optics fabrication within the context of microelectronics fabrication.

Within the preferred embodiment of the present invention, it is intended to move the wedges 38a and 38b with respect to each other such that the gap 40 is changed and the distance of travel of the further refracted refracted transmitted inspection light beam 32a and the further refracted reflected refracted transmitted inspection light beam 34a is optimized with respect to an optical parameters such as but not limited to an optical intensity parameter, an optical separation parameters or (most preferably) an optical interference parameter, which is typically employed when aligning the reticle 10 whose schematic cross-sectional diagram is illustrated in FIG. 2 within a photoexposure apparatus. Further it is also intended within the preferred embodiment of the present invention to alternatively correlate for a specific reticle, such as the reticle 10 whose schematic cross-sectional diagram is illustrated in FIG. 2, a distance of the gap 40 with the angle of incidence θ2 of the incident inspection light beam 30 such that optimal alignment of the reticle 10 whose schematic cross-sectional diagram is illustrated in FIG. 2 may be effected solely with a variation of angle of incidence of the incident alignment light beam 16 as illustrated in the schematic cross-sectional diagram of FIG. 1. Given such a correlation, which may be effected while employing the apparatus whose schematic cross-sectional diagram is illustrated in FIG. 2, proper and optimal alignment of the reticle whose schematic cross-sectional diagram is illustrated in FIG. 1 may be effected while employing a change in angle of incidence θ1 of the incident alignment light beam 16 as illustrated within the schematic cross-sectional diagram of FIG. 1 when aligning the reticle 10 as illustrated within the schematic cross-sectional diagram of FIG. 1 within a photoexposure apparatus.

As is understood by a person skilled in the art, the preferred embodiment of the present invention is illustrative of the present invention rather than limiting of the present invention. Revisions and modifications may be made to materials, structure and dimensions through which is fabricated and employed an apparatus in accord with the preferred embodiment of the present invention while still providing a method and apparatus in accord with the present invention, further in accord with the accompanying claims.

What is claimed is:

1. A method for inspecting a reticle comprising:
   providing a reticle comprising a transparent substrate having formed thereupon a patterned non-transparent layer which defines an alignment mark;
   impinging at a non-orthogonal angle through the alignment mark within the reticle an inspection light beam which is both: (a) refracted and transmitted directly through the reticle; and (b) refracted, reflected and then transmitted through the reticle, to thus provide a multiplicity of refracted transmitted inspection light beams;
   passing the multiplicity of refracted transmitted inspection light beams through a pair of transparent wedges whose inclined surfaces are counter-opposed and separated by a gap to form a series of additionally refracted transmitted inspection light beams; and
   varying a distance of the gap to optimize an optical characteristic of the additionally refracted transmitted inspection light beams.

2. The method of claim 1 further comprising correlating a variation of the distance of the gap to a variation of the non-orthogonal angle to provide a varied non-orthogonal angle which alternatively optimizes the optical characteristic of the additionally refracted transmitted inspection light beams.

3. The method of claim 1 wherein the reticle is employed for fabricating a microelectronic fabrication selected from the group consisting of integrated circuit microelectronic fabrications, ceramic substrate microelectronic fabrications, solar cell optoelectronic microelectronic fabrications, sensor image array optoelectronic microelectronic fabrications and display image array optoelectronic microelectronic fabrications.

4. The method of claim 1 wherein each of a pair of counter-opposed surfaces of the pair of wedges which is separated by the gap has an anti-reflective coating formed thereupon.

5. The method of claim 1 wherein the gap is continuously variable for a distance of from about 0.001 to about 0.7 millimeters.

6. The method of claim 1 wherein the optical characteristic is selected from the group consisting of an optical interference characteristic, an optical intensity characteristic and an optical spacing characteristic.

7. A method for forming a microelectronic layer comprising:
- providing a reticle comprising a transparent substrate having formed thereupon a patterned non-transparent layer which defines an alignment mark;
- impinging at a non-orthogonal angle through the alignment mark within the reticle an inspection light beam which is both: (a) refracted and transmitted directly through the reticle; and (b) refracted, reflected and then transmitted through the reticle, to thus provide a multiplicity of refracted transmitted inspection light beams;
- passing the multiplicity of refracted transmitted inspection light beams through a pair of wedges whose inclined surfaces are counter-opposed and separated by a gap to form a series of additionally refracted transmitted inspection light beams;
- varying a distance of the gap to optimize an optical characteristic of the additionally refracted transmitted inspection light beams;
- correlating the variation of the distance of the gap to a variation of the non-orthogonal angle to provide a varied non-orthogonal angle which alternatively optimizes the optical characteristic of the additionally refracted transmitted inspection light beams; and
- employing the reticle within a photoexposure apparatus employed for forming a patterned photoresist layer upon a substrate, wherein the reticle is aligned within the photoexposure apparatus while employing an alignment light beam at the varied non-orthogonal angle.

8. The method of claim 7 wherein the reticle is employed for fabricating a microelectronic fabrication selected from the group consisting of integrated circuit microelectronic fabrications, ceramic substrate microelectronic fabrications, solar cell optoelectronic microelectronic fabrications, sensor image array optoelectronic microelectronic fabrications and display image array optoelectronic microelectronic fabrications.

9. The method of claim 7 wherein each of a pair of inclined surfaces of the pair of wedges which is separated by the gap has an anti-reflective coating formed thereupon.

10. The method of claim 7 wherein the gap is continuously variable for a distance of from about 0.001 to about 0.7 millimeters.

11. The method of claim 7 wherein the optical characteristic is selected from the group consisting of an optical interference characteristic, an optical intensity characteristic and an optical spacing characteristic.

12. An apparatus for inspecting a reticle comprising:
- an inspection light source positioned to provide an inspection light beam at a non-orthogonal angle through an alignment mark within a reticle positioned within the apparatus, wherein the inspection light beam is both: (a) refracted and transmitted directly through the reticle; and (b) refracted, reflected and then transmitted through the reticle, to thus provide a multiplicity of refracted transmitted inspection light beams;
- a pair of transparent wedges whose inclined surfaces are counter-opposed surfaces and separated by a gap, where the pair of transparent wedges is positioned such as to pass the multiplicity of refracted transmitted inspection light beams through the pair of wedges to form a series of additionally refracted transmitted inspection light beams;
- means for varying a distance of the gap to optimize an optical characteristic of the additionally refracted transmitted inspection light beams; and
- an optical detector for detecting the optical characteristic of the additionally refracted transmitted inspection light beams.

13. The apparatus of claim 12 wherein the reticle is employed for fabricating a microelectronic fabrication selected from the group consisting of integrated circuit microelectronic fabrications, ceramic substrate microelectronic fabrications, solar cell optoelectronic microelectronic fabrications, sensor image array optoelectronic microelectronic fabrications and display image array optoelectronic microelectronic fabrications.

14. The apparatus of claim 12 wherein each of inclined surfaces of the pair of wedges which is separated by the gap has an anti-reflective coating formed thereupon.

15. The apparatus of claim 12 wherein the gap is continuously variable for a distance of from about 0.001 to about 0.7 millimeters.

16. The apparatus of claim 12 wherein the optical characteristic is selected from the group consisting of an optical interference characteristic, an optical intensity characteristic and an optical spacing characteristic.

* * * * *